US010500408B2

(12) United States Patent
Helekar et al.

(10) Patent No.: US 10,500,408 B2
(45) Date of Patent: *Dec. 10, 2019

(54) METHOD AND APPARATUS FOR PROVIDING TRANSCRANIAL MAGNETIC STIMULATION (TMS) TO A PATIENT

(71) Applicants: The Methodist Hospital, Houston, TX (US); Cornell University, Ithaca, NY (US)

(72) Inventors: Santosh A. Helekar, Sugar Land, TX (US); Henning U. Voss, New York, NY (US)

(73) Assignees: THE METHODIST HOSPITAL, Houston, TX (US); CORNELL UNIVERSITY, Ithaca, NY (US)

( * ) Notice: Subject to any disclaimer, the term of this patent is extended or adjusted under 35 U.S.C. 154(b) by 206 days.

This patent is subject to a terminal disclaimer.

(21) Appl. No.: 15/281,475

(22) Filed: Sep. 30, 2016

(65) Prior Publication Data

US 2017/0136255 A1    May 18, 2017

Related U.S. Application Data

(63) Continuation of application No. 13/829,349, filed on Mar. 14, 2013, now Pat. No. 9,456,784.

(51) Int. Cl.
*A61N 2/00* (2006.01)
*A61B 5/04* (2006.01)
(Continued)

(52) U.S. Cl.
CPC ............... *A61N 2/006* (2013.01); *A42B 1/04* (2013.01); *A42B 1/242* (2013.01);
(Continued)

(58) Field of Classification Search
CPC ... A61B 5/6803; A61B 5/0476; A61B 5/4836; A61B 5/0478; A61B 5/04008;
(Continued)

(56) References Cited

U.S. PATENT DOCUMENTS 4,537,198 A * 8/1985 Corbett ............... A61B 5/0478
600/383
4,967,038 A    10/1990 Gevins et al.
(Continued)

FOREIGN PATENT DOCUMENTS

CN    2796743      7/2006
CN    105188844    12/2015
(Continued)

OTHER PUBLICATIONS

Amassian, V. E et al., Transcranial Magnetic Stimulation in Study of the Visual Pathway, Journal of Clinical Neurophysiology, 1998, 15(4): 288-304.
(Continued)

*Primary Examiner* — Navin Natnithithadha
*Assistant Examiner* — Sunita Reddy
(74) *Attorney, Agent, or Firm* — Marshall, Gerstein & Borun LLP

(57) ABSTRACT

Apparatus for applying Transcranial Magnetic Stimulation (TMS) to a patient comprising a head mount for disposition on the head of a patient, and a plurality of magnet assemblies for releasable mounting on the head mount. The magnet assemblies comprises a magnet for selectively providing a rapidly changing magnetic field capable of inducing weak electric currents for modifying the natural electrical activity of the brain of the patient. The number of magnet assemblies mounted, their individual positioning, and their selective provision of a rapidly changing magnetic field is selected to allow spatial, strength and temporal characteristics of the
(Continued)

magnetic field to be tailored for the patient, to provide patient-specific IMS therapy, assist in diagnosis, or map out brain function. The magnet assembles can comprise magnets for provide a rapidly changing magnetic field of at least 500-600 Tesla/second corresponding to a magnet movement speed of no less than 400 Hertz.

22 Claims, 7 Drawing Sheets

(51) Int. Cl.

| | | |
|---|---|---|
| A42B 1/04 | (2006.01) | |
| A61B 5/00 | (2006.01) | |
| A61B 5/0476 | (2006.01) | |
| A61N 2/12 | (2006.01) | |
| A42B 1/24 | (2006.01) | |
| A61B 5/0478 | (2006.01) | |

(52) U.S. Cl.
CPC ........ *A61B 5/04008* (2013.01); *A61B 5/0476* (2013.01); *A61B 5/0478* (2013.01); *A61B 5/4836* (2013.01); *A61B 5/6803* (2013.01); *A61N 2/12* (2013.01); *A41D 2300/32* (2013.01); *A61B 2503/42* (2013.01)

(58) Field of Classification Search
CPC ...... A61B 2503/42; A61N 2/006; A61N 2/12; A42B 1/04; A42B 1/242; A41D 2300/32
USPC .................................. 600/13, 14, 15, 9, 544
See application file for complete search history.

(56) References Cited

U.S. PATENT DOCUMENTS

| | | | |
|---|---|---|---|
| 6,032,677 | A | 3/2000 | Blechman et al. |
| 6,123,657 | A | 9/2000 | Ishikawa et al. |
| 6,488,617 | B1 | 12/2002 | Katz |
| 7,013,177 | B1 | 3/2006 | Whitehurst et al. |
| 8,888,672 | B2 | 11/2014 | Phillips et al. |
| 9,272,159 | B2 | 3/2016 | Phillips et al. |
| 9,456,784 | B2 | 10/2016 | Helekar et al. |
| 2002/0151760 | A1* | 10/2002 | Paturu ...................... A61F 5/41 600/15 |
| 2004/0193001 | A1 | 9/2004 | Miller |
| 2006/0015153 | A1 | 1/2006 | Gliner et al. |
| 2006/0094924 | A1 | 5/2006 | Riehl |
| 2006/0265022 | A1 | 11/2006 | John et al. |
| 2007/0093706 | A1 | 4/2007 | Gevins et al. |
| 2008/0014285 | A1* | 1/2008 | Di Mauro ............ A61K 31/425 424/617 |
| 2008/0312706 | A1 | 12/2008 | Zangen et al. |
| 2009/0082690 | A1 | 3/2009 | Phillips et al. |
| 2010/0185042 | A1 | 7/2010 | Schneider et al. |
| 2010/0210894 | A1* | 8/2010 | Pascual-Leone ........ A61N 2/02 600/14 |
| 2010/0249488 | A1* | 9/2010 | Kardos .................. A61N 2/002 600/14 |
| 2011/0034822 | A1* | 2/2011 | Phillips .................. A61B 5/048 600/544 |
| 2011/0105826 | A1* | 5/2011 | Mishelevich .......... A61N 2/006 600/13 |
| 2011/0112427 | A1* | 5/2011 | Phillips .................. A61B 5/048 600/544 |
| 2011/0118536 | A1 | 5/2011 | Phillips et al. |
| 2011/0118636 | A1 | 5/2011 | Kitamura et al. |
| 2011/0184223 | A1 | 7/2011 | Peterchev et al. |
| 2011/0270345 | A1* | 11/2011 | Johnston ............ A61N 1/36025 607/45 |
| 2012/0157752 | A1 | 6/2012 | Nishikawa et al. |
| 2013/0137918 | A1 | 5/2013 | Phillips et al. |
| 2014/0163305 | A1* | 6/2014 | Watterson ................ A61N 2/12 600/14 |
| 2014/0179980 | A1 | 6/2014 | Phillips et al. |
| 2014/0200388 | A1 | 7/2014 | Schneider et al. |
| 2014/0276182 | A1 | 9/2014 | Helekar et al. |
| 2016/0193476 | A1 | 7/2016 | Helekar et al. |

FOREIGN PATENT DOCUMENTS

| | | |
|---|---|---|
| DE | 102011050507 | 11/2012 |
| WO | WO 2005/051306 | 6/2005 |
| WO | WO 2009/036040 | 3/2009 |
| WO | WO-2012/126044 A1 | 9/2012 |
| WO | WO 2014/152827 | 9/2014 |
| WO | WO 2015/023980 | 2/2015 |

OTHER PUBLICATIONS

Azañón, E. et al., Somatosensory processing and body representation, Cortex 45, 2009, 1078-1084.

Beauchamp, M. S. et al., fMRI-Guided Transcranial Magnetic Stimulation Reveals That the Superior Temporal Sulcus Is a Cortical Locus of the McGurk Effect, The Journal of Neuroscience, 2010, 30(7): 2414-7.

Beckers, G. et al., Cerebral visual motion blindness: transitory akinetopsia induced by transcranial magnetic stimulation of human area V5, Proceedings: Biological Sciences, 1992, 249(1325): 173-8.

Buch, E. R. et al., Noninvasive Associative Plasticity Induction in a Corticocortical Pathway of the Human Brain, The Journal of Neuroscience, 2011, 31(48): 17669-79.

Dayan, Eran et al., Noninvasive brain stimulation: from physiology to network dynamics and back, Nature Neuroscience, Jul. 2013, vol. 16, No. 7.

De Pasquale et al., A Cortical Core for Dynamic Integration of Functional Networks in the Resting Human Brain, Neuron, 2012, 74(4): 753-64.

De Ridder, D. et al., Primary and Secondary Auditory Cortex Stimulation for Intractable Tinnitus, ORL, 2006, 68(1): 48-54.

Deco, G. et al., Ongoing Cortical Activity at Rest: Criticality, Multistability, and Ghost Attractors, The Journal of Neuroscience, 2012, 32(10): 3366-75.

Dell'Osso, B. et al., Meta-Review of Metanalytic Studies with Repetitive Transcranial Magnetic Stimulation (rTMS) for the Treatment of Major Depression, Clinical Practice & Epidemiology in Mental Health, 2011, 7, 167-77.

Delvendahl, I. et al., Plasticity of motor threshold and motor-evoked potential amplitude—A model of intrinsic and synaptic plasticity in human motor cortex?, Brain Stimulation 5, 2012, 586-593.

Devlin, J. T. et al., Stimulating language: insights from TMS, Brain, 2007, 130, 610-22.

Fitzgerald, P. B. et al., GABA and cortical inhibition in motor and non-motor regions using combined TMS-EEG: A time analysis, Clinical Neurophysiology 120, 2009, 1706-1710.

Fox, M. D. et al., The human brain is intrinsically organized into dynamic, anticorrelated functional networks, Proceedings of the National Academy of Sciences of the USA, 2005, vol. 102, No. 27, 9673-8.

Guse, B. et al., Cognitive effects of high-frequency repetitive transcranial magnetic stimulation: a systematic review, Journal of Neural Transmission, 2010, 117: 105-22.

Helekar. S.A. et al., Electromyographic motor-evoked potentials elicited by transcranial magnetic stimulation with rapidly moving permanent magnets mounted on a multisite stimulator cap, Presentation Abstract, Nov. 13, 2013.

Helekar, S.A. et al., Electromyographic motor-evoked potentials elicited by TMS with rapidly moving permanent magnets mounted on a multisite stimulator cap, 2013.

Helekar, Santosh A., In Defense of Experience—Coding Nonarbitrary Temporal Neural Activity Patterrns, Consciousness and Cognition, Dec. 1999, pp. 455-461, vol. 8, Issue 4.

Helekar, Santosh A., On the Possibility of Universal Neural Coding of Subjective Experience, Consciousness and Cognition, Dec. 1999, pp. 423-446, vol. 8, Issue 4.

(56) References Cited

OTHER PUBLICATIONS

Huerta, P. T. et al., Transcranial magnetic stimulation, synaptic plasticity and network oscillations, Journal of NeuroEngineering and Rehabilitation, 2009, 6:7.
Ilic, T. V. et al., Exploring Motor Cortical Plasticity Using Transcranial Magnetic Stimulation in Humans, Annals of the New York Academy of Sciences, 2005, vol. 1048(1): 175-184.
Kamitani, Y. et al., Manifestation of scotomas created by transcranial magnetic stimulation of human visual cortex, Nature Neuroscience, 1999, 2(8): 767-71.
Kamke, M. R. et al., Parietal disruption alters audiovisual binding in the sound-induced flash illusion, NeuroImage 62, 2012, 1334-1341.
Kammer, T., Masking visual stimuli by transcranial magnetic stimulation, Psychological Research, 2007, 71: 659-66.
Leuchter, A. F. et al., Synchronized Transcranial Magnetic Stimulation (sTMS) Efficacy and Safety of Low-field Synchronized Transcranial Magnetic Stimulation (sTMS) for Treatment of Major Depression, Brain Stimulation, 2015, 1-8.
Levasseur-Moreau, J. et al., Translational application of neuromodulation of decision-making, Brain Stimulation 5, 2012, 77-83.
Lipton, R. B. et al., Transcranial Magnetic Simulation in the Treatment of Migraine, Neurotherapeutics: The Journal of the American Society for Experimental NeuroTherapeutics, 2010, vol. 7, 204-12.
Muller, P. A. et al., Safety and tolerability of repetitive transcranial magnetic stimulation in patients with pathologic positive sensory phenomena: a review of literature, Brain Stimulation, 2012, 5(3): 320-329.
Müller-Dahlhaus, F. et al., Plasticity resembling spike-timing dependent synaptic plasticity: the evidence in human cortex, Frontiers in Synaptic Neuroscience, 2010, vol. 2, Article 34, 1-11.
Nakatani-Enomoto, S. et al., Bidirectional modulation of sensory cortical excitability by quadripulse transcranial magnetic stimulation (QPS) in humans, Clinical Neurophysiology 123, 2012, 1415-1421.
Pitcher, D. et al., Transcranial Magnetic Stimulation Disrupts the Perception and Embodiment of Facial Expressions, The Journal of Neuroscience, 2008, 28(36): 8929-33.
Rossi S. et al., Safety, ethical considerations, and application guidelines for the use of transcranial magnetic stimulation in clinical practice arid research, Clinical Neurophysiology, 2009, 2008-2039.
Sanchez, Alvaro et al., Antimagnets: Controlling Magnetic Fields With Superconductor-Metamaterial Hybrids, New Journal of Physics; 2011, vol. 2013.
Sandrini, M. et al., The use of transcranial magnetic stimulation in cognitive neuroscience: A new synthesis of methodological issues, Neuroscience and Biobehavioral Reviews 35, 2011, 516-536.
Wassermann, E. M. et al., Transcranial Magnetic Brain Stimulation: Therapeutic Promises and Scientific Gaps, Pharmacology and Therapeutics, 2012, 133(1): 98-107.
Wassermann, E. M., Risk and safety of repetitive transcranial magnetic stimulation: report and suggested guidelines from the International Workshop on the Safety of Repetitive Transcranial Magnetic Stimulation, Jun. 5-7, 1996, Electroencephalography and Clinical Neurophysiology, 1998, 108, 1-16.
Helekar, Santosh et al., Transcranial Brain Stimulation With Rapidly Spinning High-Field Permanent Magnets, IEEE Access, vol. 4, May 19, 2016, pp. 2520-2527.
Aleman, A., Use of Repetitive Transcranial Magnetic Stimulation for Treatment in Psychiatry, Clinical Psychopharmacology and Neuroscience, 2013, vol. 11, No. 2, pp. 53-59.
Antal, A. et al., Electrical Stimulation and Visual Network Plasticity, Restorative Neurology and Neuroscience, 2011, vol. 29, pp. 365-374.
Bikson, M. et al., Effects of Uniform Extracellular DC Electric Fields on Excitabiity in Rai Hippocampal Slices in Vitro, Journal of Physiology, 2004, vol. 557, pp. 175-190.
Cardenas-Morales, L. et al., Mechanisms and Applications of Theta-Burst rTMS on the Human Motor Cortex, Brain Topogr, 2010, Voi. 22, pp. 294-306.
Chen, R. et al., The Clinical Diagnostic Utility of Transcranial Magnetic Stimulation: Repost of an IFCN Committee, Clinical Neurophysiology, 2008, Voi. 119, pp. 504-532.
Deans, J.K. et al,, Sensitivity of Coherent Oscillations in Rat Hippocampus to AC Electric Fields, Journal of Physiology, 2007, vol. 583, pp. 555-565.
Esser, S.K. et al., Modeling the Effects of Transcranial Magnetic Stimulation on Cortical Circuits, Journal of Physiology, 2005, vol. 94, pp. 622-639.
Farina, D. et al., Detecting the Unique representation of the Motor-Unit Action Potentials in the Surface Electromyogram, Journal of Neurophysiology, 2008, vol. 100, pp. 1223-1233.
Fregni, F. et al., Technology Insight: NonInvasice Brain Stimulation in Neurology: Perspectives on the Therapeutic Potential of rTMS and tDCS, Nature Clinical Practice Neurology, 2007, vol. 3, pp. 1-11.
Frohlich, F. et al., Endogenous Electric Fields May Guide Neocorticai Network Activity, Neuron, Jul. 15, 2010, Voi. 67, pp. 129-143.
Frye, R.E. et al., Transcrania! Magnetic Stimulation in Child Neurology: Current and Future Directions, Journal of Child Neurology, Jan. 2008, vol. 23, No. 1, pp. 79-96.
George, M.S. et al,, The Expanding Evidence Base for rTMS Treatment of Depression, Current Opinion on Psychiatry, Jan. 2013, vol. 26, No. 1, pp. 13-18.
Gonzalez-Rosa, J.J. et al.., Static Magnetic Field Stimulation over the Visual Cortex increases Alpha Oscillations and Slows Visual Search in Humans, The Journal of Neuroscience, Jun. 17, 2015, Voi. 35, No. 24, pp. 9182-9193.
Helfrich, R.F. et al., Entrainment of Brain Oscillations by Transcranial Alternating Current Stimulation, Current Biology, Feb. 3, 20147, vol. 24, pp. 333-339.
Jin, Y. et al., A Pilot Study of the Use of EEG-Based Synchornlzed Transcranial Magnetic Stimulation (sTMS) for Treatment of Major Depression, BMC Psychiatry, 2014, Voi. 14, No. 13, pp. 1-6.
Di Lazzaro, V. et al., Modulation of Motor Cortex Neuronal Networks by rTMS: Comparison of Local and Remote Effects of Six Different Protocols of Stimulation, Journal of Neurophysiology, 2011, vol. 105, pp. 2150-2156.
Olivierg, A. et al., Transcranial Static Magnetic Field Stimulation of the Human Motor Cortex, Journal of Physiology, 2011, vol. 589, No. 20, pp. 4949-4958.
Rivadulla, C. et al., Magnetic Field Strength and Reproducibility of Neodymium Magnets Usefui for Transcranial Static Magnetic Field Stimulation of the Human Cortex, Neuromodulation: Technology at the Neural interface, 2014, vol. 17, No. 5, pp. 438-442.
Thielscher, A, et al., Linking Physics with Physiology in TMS: A Sphere Field Model to Determine the Cortical Stimulation Site in TMS, Neuroimage, 2002, vol. 17, pp. 1117-1130.
Zaehle, T. et al., Transcranial Alternating Current Stimulation Enhances Individual Alpha Activity in Human EEG, PloS one, Nov. 2010, vol. 5, No. 11, pp. 1-7.
Extended European Search Report for Application No. 14836452.4, dated May 2, 2017.
First Office Action for Chinese Application No. 201480057016.4, dated May 28, 2018.
International Search Report and Written Opinion for Application No. PCT/US2014/051340, dated Apr. 15, 2015.
International Preliminary Report on Patentability for Application No. PCT/US2014/051340, dated Feb. 16, 2016.
International Search Report and Written Opinion for Application No. PCT/US2014/027900, dated Sep. 4, 2014.
International Preliminary Report on Patentability for Application No. PCT/US2014/027900, dated Sep. 15, 2015.
Extended European Search Report for Application No. 14771163.4, dated Jan. 3, 2017.
Third Office Action for Chinese Application No. 201480027788.3, dated Mar. 6, 2018.
Second Office Action for Chinese Application No. 201480027788.3, dated Aug. 14, 2017.

(56) References Cited

OTHER PUBLICATIONS

First Office Action for Chinese Application No. 201480027788.3, dated Oct. 10, 2016.
International Search Report and Written Opinion for Application No. PCT/US2017/031413, dated Aug. 14, 2017.
International Preliminary Report on Patentability for Application No. PCT/US2017/031413, dated Nov. 15, 2018.
Office Action, European Patent Application No. 14771163.4, dated Mar. 20, 2019.

* cited by examiner

COMPARISON OF PRESENT INVENTION WITH CONVENTIONAL TMS

| | Present Invention | Conventional TMS |
|---|---|---|
| Type of Magnet | Permanent Neodymium | Electromagnetic Coil |
| Maximum Field Strength | 1.48 T | 2.2 T |
| dB/dt | 500 – 5000 T/s | 5000 – 20,000 T/s |
| Stimulus Duration | 1 – 100 ms | 0.3 – 5 ms |
| Repetition Rate | 0.1 – 2 Hz | 0.1 – 50 Hz |
| Stimulation Sites | Multiple (1 – 32) | Single |
| Dynamic Modification | Present | Absent |
| User Interaction | Present | Absent |
| Current for Stimulation | None | 4000 A |
| Power Supply | DC Battery (9 – 12 V) | AC Main (110 – 220 V) |
| Risk of Electric Shock | Absent | Present |
| Risk of Burns | Absent | Present |
| Risk of Seizure | Absent | Present at high rates |

FIG. 6

METHOD AND APPARATUS FOR PROVIDING TRANSCRANIAL MAGNETIC STIMULATION (TMS) TO A PATIENT

This Application is a Continuation of application Ser. No. 13/829,349 filed on Mar. 14, 2013, published as U.S. Publication No. 2014/0276182 A1. The entire contents of these applications are incorporated herein by reference in their entirety.

FIELD OF THE INVENTION

This invention relates to Transcranial Magnetic Stimulation (TMS) in general, and more particularly to novel methods and apparatus for providing transcranial magnetic stimulation to a patient.

BACKGROUND OF THE INVENTION

Transcranial Magnetic Stimulation (TMS) is a non-invasive procedure in which magnetic stimulation is applied to the brain in order to modify the natural electrical activity of the brain, whereby to provide therapy to a patient, to assist in diagnosis or to map out brain function in neuroscience research. More particularly, TMS applies a rapidly changing magnetic field to the brain of a patient in order to induce weak electric currents in the brain of the patient through electromagnetic induction. These weak electric currents modify the natural electrical activity of the brain of the patient, whereby to provide therapy to the patient, to assist in diagnosis or to map out brain function in neuroscience research. TMS has been approved by the Food and Drug Administration (FDA) for treating depression. TMS is also currently being investigated in the management of various other neurological and psychiatric disorders, including stroke, migraines, Parkinson's disease, tinnitus, autism, schizophrenia, etc. TMS is also being used to study brain function in neuroscience research.

Conventional TMS apparatus generally comprises an electromagnetic coil which is fixed in position relative to the head of the patient. Since the magnetic field applied to the patient is a function of the configuration of the electromagnetic coil, the current passed through the electromagnetic coil, and the location of the electromagnetic coil relative to the patient, the fixed construction of conventional TMS apparatus significantly limits the character of the magnetic field which can be applied to the patient, and hence significantly limits the TMS therapy which can be provided to the patient. In addition, conventional TMS apparatus generally utilizes very high electric currents in the electromagnetic coil, which raises the risk of accidental injury to the patient through electric shocks, burns, seizures, etc.

The present invention addresses the foregoing problems associated with the prior art by providing an improved method and apparatus for providing Transcranial Magnetic Stimulation (TMS) to a patient. In addition, the present invention also provides additional advantages over conventional TMS, e.g., (a) it comprises a portable, wearable device that can be used outside of a medical or research facility, e.g., at home; (b) patients can self-administer a prescribed treatment regimen at home through handheld, or worn, wired or wireless electronic controllers; (c) it comprises multiple magnetic stimulators directable at multiple brain structures which can lead to better treatment, diagnostic testing or insight into brain function through its use in neuroscience research; (d) it comprises multiple magnetic stimulators directable at one and the same brain structure which can be more effective because they can induce current flow in multiple orientations; and (e) it comprises multiple magnetic stimulators which can aggregate their magnetic fields for more robust brain stimulation.

SUMMARY OF THE INVENTION

The present invention provides a novel method and apparatus for providing Transcranial Magnetic Stimulation (TMS) to a patient. Among other things, the present invention comprises the provision and use of novel TMS apparatus which allows the spatial, strength and temporal characteristics of the magnetic field generated by the TMS apparatus to be custom tailored for each patient, whereby to provide patient-specific TMS therapy or diagnostic testing. It also affords greater flexibility in open-ended investigations of brain function in neuroscience research.

In one form of the invention, there is provided apparatus for applying Transcranial Magnetic Stimulation (TMS) to a patient, wherein the apparatus comprises:

a head mount for disposition on the head of a patient; and a plurality of magnet assemblies for releasable mounting on the head mount, wherein each of the magnet assemblies comprises a magnet for selectively providing a rapidly changing magnetic field capable of inducing weak electric currents in the brain of a patient so as to modify the natural electrical activity of the brain of the patient;

wherein the number of magnet assemblies mounted on the head mount, their individual positioning on the head mount, and their selective provision of a rapidly changing magnetic field is selected so as to allow the spatial, strength and temporal characteristics of the magnetic field to be custom tailored for each patient, whereby to provide patient-specific TMS therapy or diagnostic testing, as well as greater flexibility in open-ended investigations of brain function in neuroscience research. In one preferred form of the invention, each of the magnet assemblies comprises a magnet for selectively providing a rapidly changing magnetic field of at least 500-600 Tesla/second corresponding to a magnet movement speed of no less than 400 Hertz.

In another form of the invention, there is provided a method for providing Transcranial Magnetic Stimulation (TMS) to a patient, the method comprising:

providing apparatus comprising:
a head mount for disposition on the head of a patient; and
a plurality of magnet assemblies for releasable mounting on the head mount, wherein each of the magnet assemblies comprises a magnet for selectively providing a rapidly changing magnetic field capable of inducing weak electric currents in the brain of a patient so as to modify the natural electrical activity of the brain of the patient;

positioning the head mount on the head of the patient, and positioning a selected number of magnet assemblies on the head mount at selected locations; and selectively providing a rapidly changing magnetic field with at least one of the magnet assemblies;

wherein the number of magnet assemblies mounted on the head mount, their individual positioning on the head mount, and their selective provision of a rapidly changing magnetic field is selected so as to custom tailor the spatial, strength and temporal characteristics of the magnetic field for that patient, whereby to provide patient-specific TMS therapy or diagnostic testing, as well as greater flexibility in open-ended investigations of brain function in neuroscience research. In one preferred form of the invention, each of the magnet assemblies comprises a magnet for selectively providing a rapidly changing magnetic field of at least 500-600 Tesla/second corresponding to a magnet movement speed of no less than 400 Hertz.

In another form of the invention, there is provided apparatus for applying Transcranial Magnetic Stimulation (TMS) to a patient, wherein the apparatus comprises:

a head mount for disposition on the head of a patient; and a plurality of magnet assemblies mounted on the head mount in a predetermined pattern, wherein each of the magnet assemblies comprises a magnet for selectively providing a rapidly changing magnetic field capable of inducing weak electric currents in the brain of a patient so as to modify the natural electrical activity of the brain of the patient;

wherein the number of magnet assemblies mounted on the head mount, their individual positioning on the head mount, and their selective provision of a rapidly changing magnetic field is selected so as to allow the spatial, strength and temporal characteristics of the magnetic field to be custom tailored for each patient, whereby to provide patient-specific TMS therapy, to assist in diagnosis or to map out brain function in neuroscience research. In one preferred form of the invention, each of the magnet assemblies comprises a magnet for selectively providing a rapidly changing magnetic field of at least 500-600 Tesla/second corresponding to a magnet movement speed of no less than 400 Hertz.

In another form of the invention, there is provided a method for providing Transcranial Magnetic Stimulation (TMS) to a patient, the method comprising:

providing apparatus comprising:
a head mount for disposition on the head of a patient; and
a plurality of magnet assemblies mounted on the head mount in a predetermined pattern, wherein each of the magnet assemblies comprises a magnet for selectively providing a rapidly changing magnetic field capable of inducing weak electric currents in the brain of a patient so as to modify the natural electrical activity of the brain of the patient;

positioning the head mount on the head of the patient; and selectively providing a rapidly changing magnetic field with at least one of the magnet assemblies;

wherein the number of magnet assemblies mounted on the head mount, their individual positioning on the head mount, and their selective provision of a rapidly changing magnetic field is selected so as to custom tailor the spatial, strength and temporal characteristics of the magnetic field for that patient, whereby to provide patient-specific TMS therapy, to assist in diagnosis or to map out brain function in neuroscience research. In one preferred form of the invention, each of the magnet assemblies comprises a magnet for selectively providing a rapidly changing magnetic field of at least 500-600 Tesla/second corresponding to a magnet movement speed of no less than 400 Hertz.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 6 is a table illustrating some of the advantages of the present invention over conventional TMS.

DETAILED DESCRIPTION OF THE PREFERRED EMBODIMENTS

Figure 1:
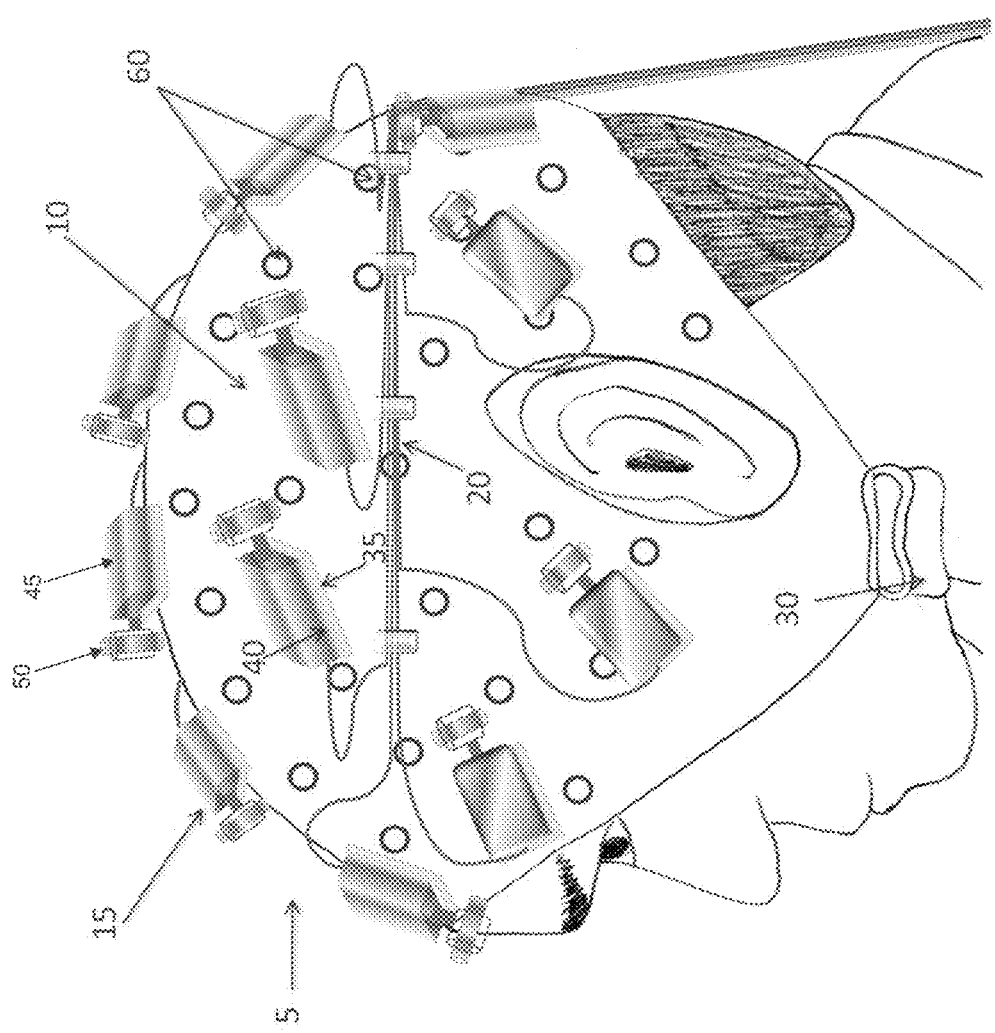
FIGS. 1 and 2 are schematic views illustrating novel apparatus for providing Transcranial Magnetic Stimulation (TMS) to a patient.
Figure 2:
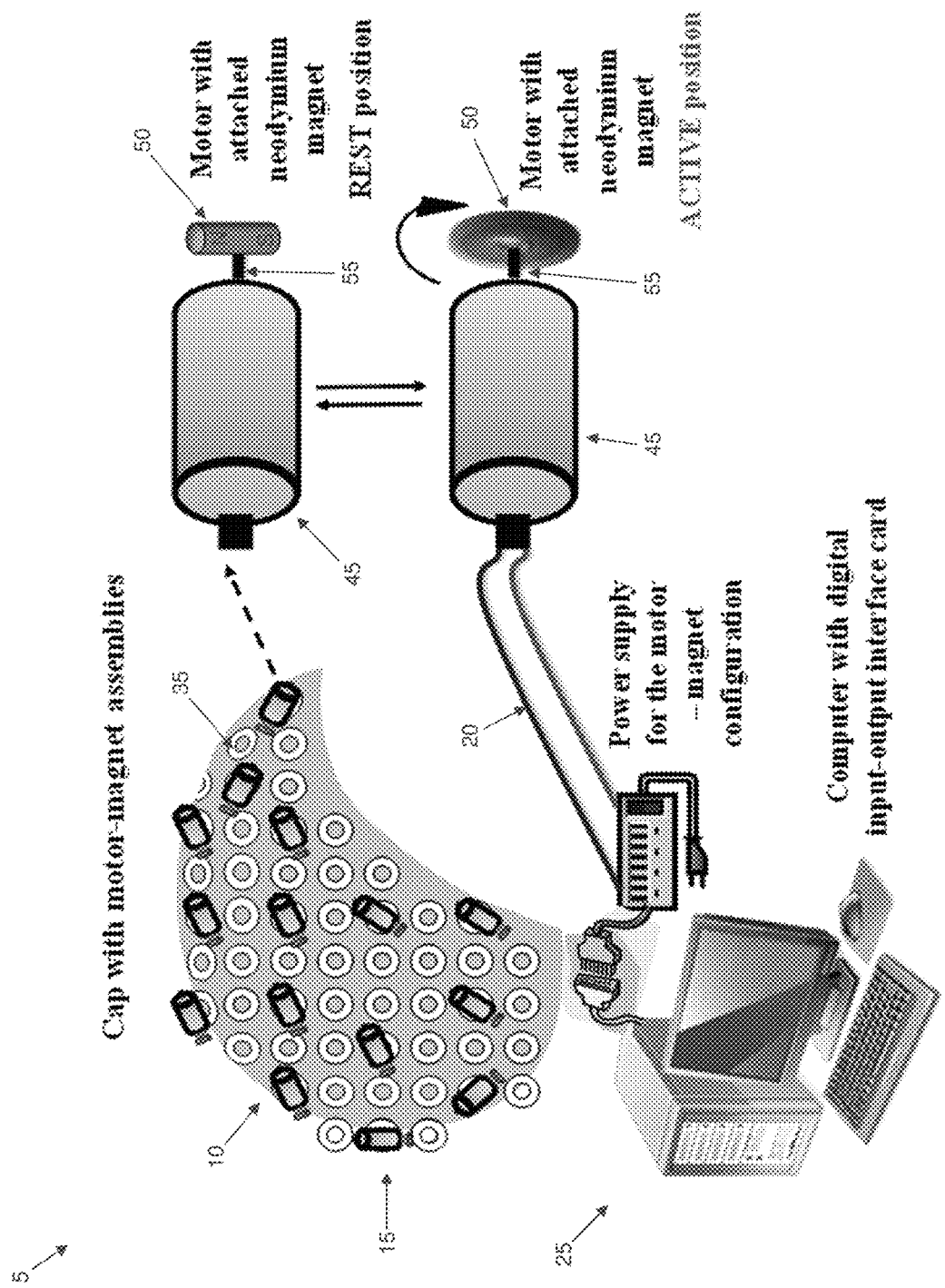

Looking first at FIGS. 1 and 2, there is shown novel Transcranial Magnetic Stimulation (TMS) apparatus 5 for providing TMS to a patient. Among other things, and as will hereinafter be discussed, novel TMS apparatus 5 allows the spatial, strength and temporal characteristics of the magnetic field generated by the TMS apparatus to be custom tailored for each patient, whereby to provide patient-specific TMS therapy, to assist in diagnosis or to map out brain function in neuroscience research.

More particularly, TMS apparatus 5 generally comprises a head mount 10 for positioning on the head of a patient, a plurality of magnet assemblies 15 which are releasably mounted to head mount 10, and a plurality of leads 20 for connecting each of the magnet assemblies 15 to a computerized controller 25. Computerized controller 25 may be a self-standing device or, if desired, computerized controller 25 may be wearable, e.g., on a waistband, an armband, etc. Additionally, if desired, magnet assemblies 15 may be connected to computerized controller 25 wirelessly, whereby to eliminate the need for leads 20.

In one preferred form of the invention, head mount 10 comprises a soft, form-fitting skull cap adapted to cover the head of the patient while leaving the face and ears of the patient exposed. Head mount 10 is intended to provide a stable support for the aforementioned magnet assemblies 15, and to that end head mount 10 preferably comprises a textile construct (e.g., woven, braided or knit fibers) that has a stable structure but which can breathe (for patient comfort). Alternatively, the head mount could be constructed of other materials such as soft plastic. Head mount 10 preferably includes a chin strap 30 so that the head mount can be fastened onto the head of a patient with light tension, whereby to ensure that the head mount maintains a fixed position on the head of the patient.

As noted above, a plurality of magnet assemblies 15 are releasably mounted to head mount 10. More particularly, magnet assemblies 15 are releasably mounted to head mount 10 so that the number of magnet assemblies 15, and/or their individual positioning on head mount 10, can be varied as desired by the clinician or investigator. To this end, head mount 10 preferably comprises a plurality of fastener bases 35 which are distributed about the outer surface of head mount 10, and each of the magnet assemblies 15 preferably comprises a counterpart fastener connect 40 adapted to mate with a fastener base 35, whereby to allow each magnet assembly 15 to be releasably secured to head mount 10 substantially anywhere about the surface of the head mount. It will be appreciated that, as a result of this construction, it is possible to releasably secure the desired number of magnet assemblies 15 to head mount 10, at the desired locations for those magnet assemblies 15, so that the number of magnet assemblies 15, and/or their positioning on head mount 10, can be varied as desired by the clinician or investigator.

By way of example but not limitation, head mount 10 may comprise a woven fabric skull cap covering the skull of the patient, the plurality of fastener bases 35 disposed on head mount 10 may each comprise one half of a conventional hook-and-loop (e.g., Velcro™) fastener, and the fastener connects 40 of the magnet assemblies 15 may each comprise the second half of a conventional hook-and-loop (e.g., Velcro™) fastener. In this way, each of the magnet assemblies 15 may be releasably fastened to a fastener base 35, and hence to head mount 10.

In one preferred form of the invention, magnet assemblies 15 each comprise a motor 45 and a permanent magnet 50. Permanent magnet 50 is mounted to the drive shaft 55 of motor 45, such that when motor 45 is energized, permanent magnet 50 will rotate, whereby to provide a rapidly changing magnetic field about the magnet assembly. In one preferred form of the invention, each of the magnet assemblies 15 comprises a permanent magnet 50 for selectively providing a rapidly changing magnetic field of at least 500-600 Tesla/second corresponding to a magnet movement speed of no less than 400 Hertz. As will be appreciated by those knowledgeable in the field of TMS, by applying this rapidly changing magnetic field of at least 500-600 Tesla/second, corresponding to magnet movement speed of no less than 400 Hertz, to the brain of a patient, weak electric currents can be induced in the neurons of the brain of the patient. These weak electric currents modify the natural electrical activity of the brain of the patient, whereby to provide therapy to the patient, to assist in diagnosis or to map out brain function in neuroscience research. In one preferred form of the invention, motor 45 is a variable speed motor, such that permanent magnet 50 may be rotated faster or slower, as desired, whereby to adjust the voltage of the electric currents induced in the neurons of the brain of the patient, as will hereinafter be discussed in further detail. In one preferred form of the invention, permanent magnet 50 comprises a rare earth magnet, e.g., a neodymium magnet.

TMS apparatus 5 also comprises a computerized controller 25 for independently controlling the operation of each of the magnet assemblies 15, i.e., turning motors 45 on or off, regulating the speeds of motor rotation, etc. Leads 20 connect computerized controller 25 to each of the magnet assemblies 15.

Figure 3:
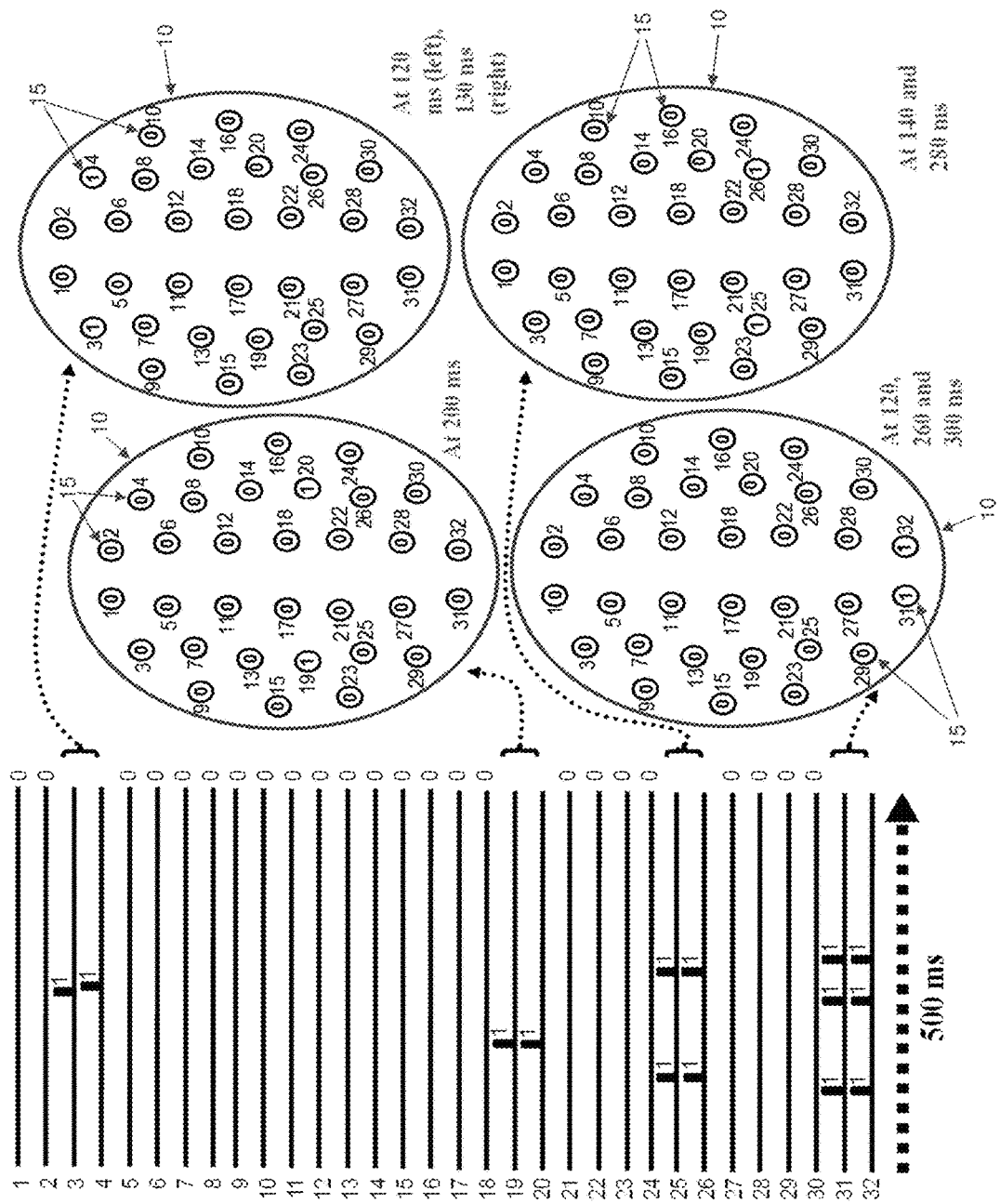
FIG. 3 is a schematic view illustrating how selective ones of the magnet assemblies of the TMS apparatus of FIGS. 1 and 2 may be activated at selected times so as to provide the desired TMS therapy to a patient, diagnostic testing or investigative protocol in neuroscience research.
Figure 4:
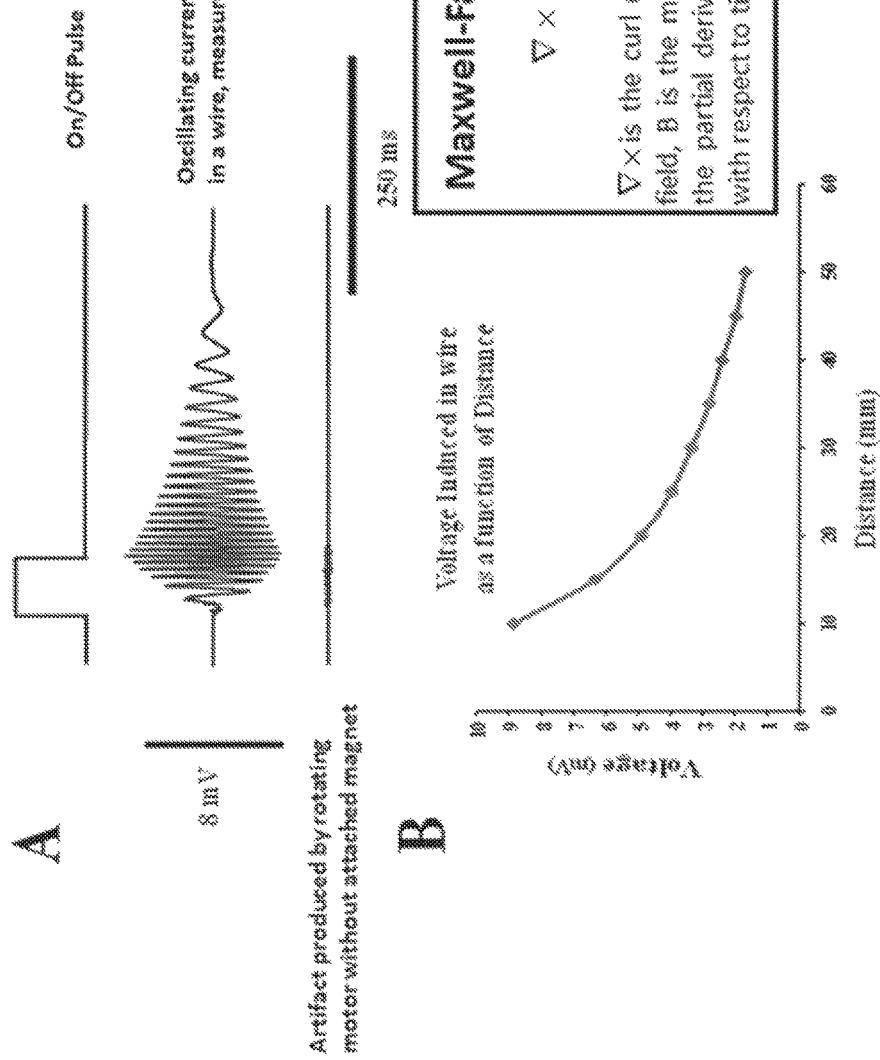
FIG. 4 is a schematic view illustrating the physics of magnetic stimulation in a conductor.
Figure 5:
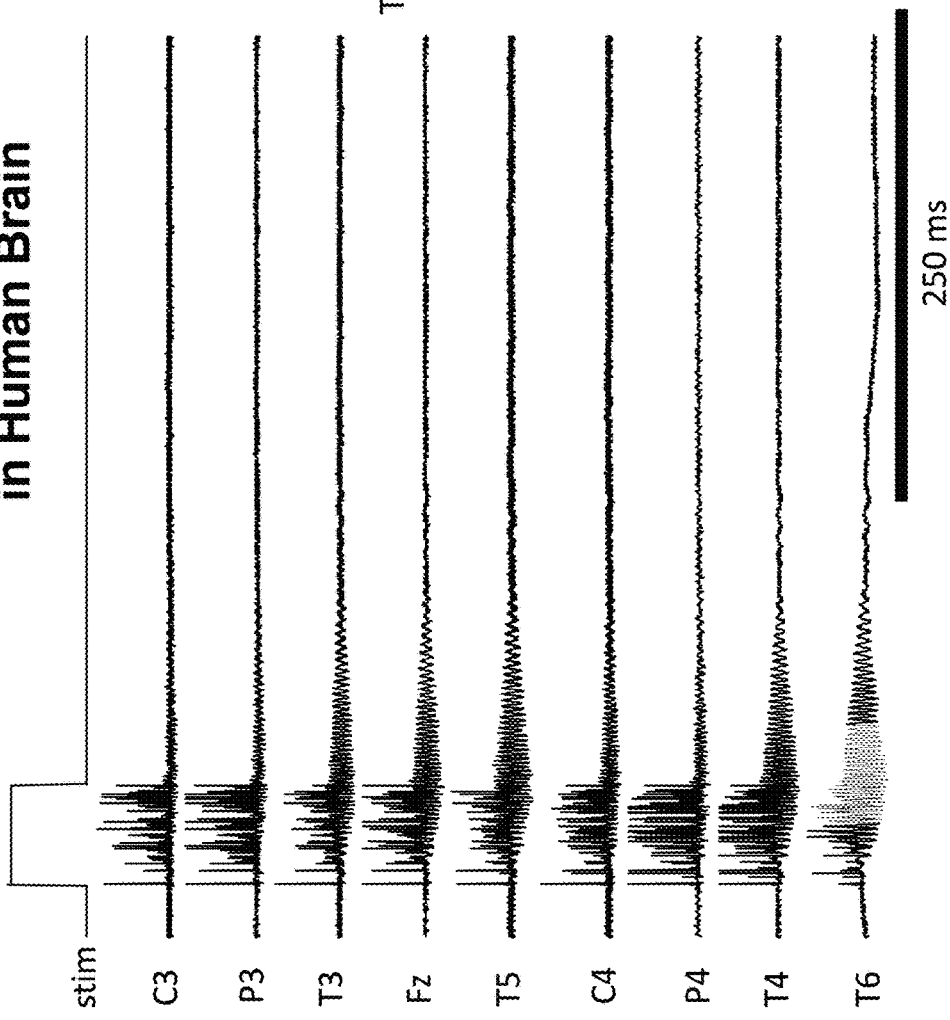
FIG. 5 is a schematic view illustrating the biophysics of magnetic stimulation of a brain.

Thus, in accordance with the present invention, a clinician or investigator first determines, for each individual patient, (i) how many magnet assemblies 15 should be mounted to head mount 10, (ii) where those magnet assemblies 15 should be mounted on head mount 10, (iii) when various magnet assemblies 15 should have their permanent magnets 50 rotated, and (iv) the speed of such rotation, in order to precisely tailor the spatial, strength and temporal characteristics of the magnetic field which is generated by TMS apparatus 5, whereby to provide that patient with patient-specific TMS therapy, to assist in diagnosis or to map out brain function in neuroscience research. Thereafter, when TMS therapy or test is to be applied to the patient, the patient puts on head mount 10, the clinician or investigator mounts the appropriate number of magnet assemblies 15 to head mount 10, positioning those magnet assemblies at the appropriate locations on head mount 10, and then computerized controller 25 thereafter controls which magnet assemblies 15 have their magnets rotated when, and at what speed. In this way, the spatial, strength and temporal characteristics of the magnetic field generated by TMS apparatus 5 can be precisely tailored according to each patient's needs, whereby to provide patient-specific TMS therapy to the patient, to assist in diagnosis or to map out brain function in neuroscience research. See, for example, FIG. 3, which shows how selected magnet assemblies 15, located at various locations about head mount 10, may have their respective permanent magnets rotated at different times. In this respect it will be appreciated that as the permanent magnet of a particular magnetic assembly 15 is rotated, it will apply a rapidly changing magnetic field to the patient, and this changing magnetic field is a function of the size and strength of the permanent magnet 50 of that magnet assembly and the rate at which the permanent magnet is rotated. See also, for example, FIG. 4, which illustrates the physics of magnetic stimulation in a conductor, and FIG. 5, which illustrates the rapid voltage fluctuations induced by magnetic stimulation in a human brain. Furthermore, it will be appreciated that the rapidly changing magnetic fields produced by the plurality of magnetic assemblies 15 located on head mount 10 together aggregate into a complex, composite, rapidly changing magnetic field which varies across the brain of the patient, both spatially and temporally, according to the positions of the magnet assemblies 15 on head mount 10 and the relative timings of their respective magnet rotations.

Thus it will be seen that with the novel TMS apparatus 5 of the present invention, the clinician or investigator may custom tailor the spatial, strength and temporal characteristics of the magnetic field generated by the TMS apparatus 5 for each patient, whereby to provide patient-specific TMS therapy, to assist in diagnosis or to map out brain function in neuroscience research.

Significantly, the present invention comprises a portable, wearable device that can be used outside of a medical or research facility, e.g., at home. Furthermore, patients can self-administer a prescribed treatment regimen at home through handheld, or worn, wired or wireless electronic controllers.

It should be appreciated that, inasmuch as the present invention comprises multiple magnetic stimulators directable at multiple brain structures, it can be possible to achieve better treatment, diagnostic testing or insight into brain function through its use in neuroscience research.

Also, inasmuch as the present invention comprises multiple magnetic stimulators directable at a single brain structure, it can be possible to achieve superior results because they can induce current flow in multiple orientations.

Furthermore, inasmuch as the present invention comprises multiple magnetic stimulators which can aggregate their magnetic fields for more robust brain stimulation, it can be possible to achieve better treatment, diagnostic testing or insight into brain function through its use in neuroscience research. Among other things, this more robust brain stimulation can relate to which regions of the brain are stimulated, the orientation(s) of the current flow induced in the regions which are stimulated, the magnitudes of the current flow induced in the regions which are stimulated, and the timings of such stimulation.

In accordance with the present invention, there is also provided a novel method for determining how many magnet assemblies 15 should be mounted to head mount 10, where those magnet assemblies 15 should be mounted on head mount 10, when various magnet assemblies 15 should have their magnets rotated, and the speed of such magnet rotation, in order to precisely tailor the spatial, strength and temporal characteristics of the magnetic field which is to be applied to that patient, whereby to provide that patient with patient-specific TMS therapy, to assist in diagnosis or to map out brain function in neuroscience research. More particularly, in accordance with the present invention, head mount 10 may include a plurality of electrodes 60 for monitoring changes in the electrical activity of the brain of the patient. Electrodes 60 are preferably connected to computerized controller 25 so that changes in the electrical activity of the brain, monitored by electrodes 60, can be correlated with variations in the spatial, strength and temporal characteristics of the magnetic field being applied to the patient by TMS apparatus 5, which in turn corresponds to the number, location and speed of rotation of the various magnet assemblies 15. In this way, using a feedback process, changes in the number, location and speed of rotation of the various magnet assemblies 15 can be correlated to changes in the electrical activity of the brain of the patient, whereby to create a patient specific TMS therapy, to assist in diagnosis or to map out brain function in neuroscience research.

The present invention offers numerous advantages over the prior art. More particularly, the novel TMS apparatus 5 of the present invention allows the spatial, strength and temporal characteristics of the magnetic field to be custom tailored for each patient, whereby to provide patient-specific TMS therapy, to assist in diagnosis or to map out brain function in neuroscience research. Among other things, the present invention provides the following significant advantages over conventional TMS: (a) it comprises a portable, wearable device that can be used outside of a medical or research facility, e.g., at home; (b) patients can self-administer a prescribed treatment regimen at home through handheld, or worn, wired or wireless electronic controllers; (c) it comprises multiple magnetic stimulators directable at multiple brain structures which can lead to better treatment, diagnostic testing or insight into brain function through its use in neuroscience research; (d) it comprises multiple magnetic stimulators directable at one and the same brain structure which can be more effective because they can induce current flow in multiple orientations; and (e) it comprises multiple magnetic stimulators which can aggregate their magnetic fields for more robust brain stimulation. In addition, the present invention eliminates the risk of accidental injury to the patient through electric shocks, burns, seizures, etc.

See FIG. 6, which lists some of the advantages of the present invention over conventional TMS apparatus.

Modifications of the Preferred Embodiments

It should be appreciated that many additional changes in the details, materials, steps and arrangements of parts, which have been herein described and illustrated in order to explain the nature of the present invention, may be made by those skilled in the art while still remaining within the principles and scope of the invention.

By way of example but not limitation, the entire outer surface of head mount 10 may be covered by a single large fastener base 35, or major sections of head mount 10 may be covered by several large fastener bases 35, where the one or more large fastener bases 35 receive one or more magnet assemblies 15.

Furthermore, if desired, head mount 10 may be formed as a harness, comprising a plurality of straps which are connected together, but have spacing between the various straps, so as to provide a grid-like structure about the head. These straps can be formed out of leather, plastic, a textile, etc. In this form of the invention, fastener bases 35, and hence magnet assemblies 15, are mounted along the straps which make up head mount 10.

Figure 7:
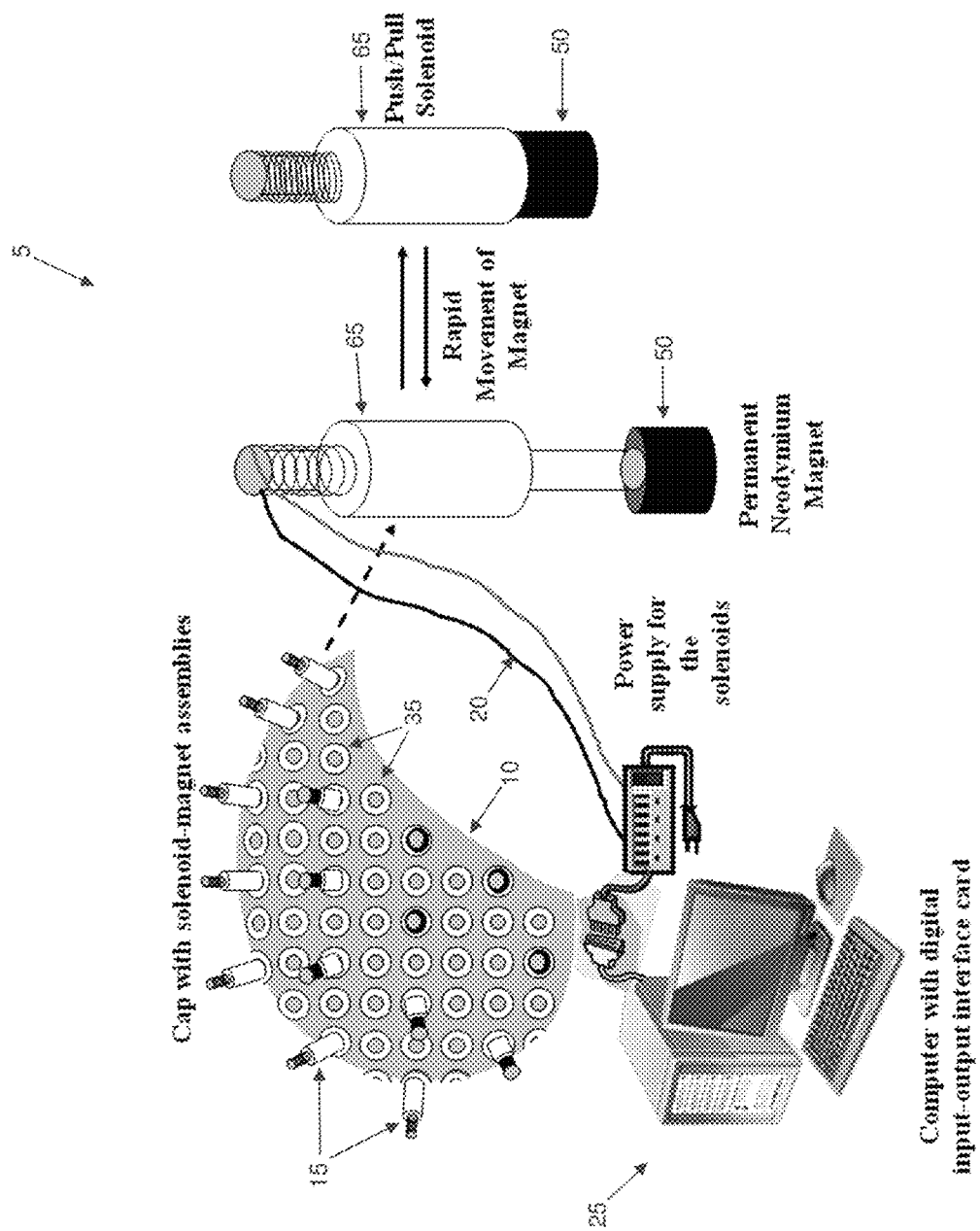
FIG. 7 is a schematic view illustrating alternative apparatus for providing TMS to a patient.

In addition, if desired, magnet assemblies 15 may be constructed so that magnets 50 are moved longitudinally, rather than rotationally, in order to produce a rapidly changing magnetic field. See, for example, FIG. 7, where solenoids 65 move magnets 50 rapidly so as to create the changing magnetic field utilized in the present invention.

Also, if desired, permanent magnets 50 may be replaced by small electromagnets, if the requisite high strength magnetic field can be achieved (e.g., so as to provide a rapid change of magnetic flux of at least 500-600 Tesla/second), and with the appropriate amount of cooling to prevent heating and melting of the magnet coils.

In accordance with the present invention, it is also possible to provide a head mount 10 (e.g., a skull cap) which has a predetermined number of magnet assemblies 15 already mounted on (or incorporated into) head mount 10 in a predetermined pattern. In this case, the clinician determines which ones of the predetermined, predisposed magnet assemblies 15 should be activated and, for those magnet assemblies which are to be activated, when they should have their magnets rotated, and the speed of such rotation, in order to precisely tailor the spatial, strength and temporal characteristics of the magnetic field which is to be applied to the patient, whereby to provide that patient with patient specific TMS therapy, to assist in diagnosis, or to map out brain function in neuroscience research. Furthermore, in this form of the invention, it may be desirable to provide a kit of such devices, wherein each device in the kit comprises a head mount 10 (e.g., a skull cap) which has a predetermined number of magnet assemblies 15 already mounted on (or incorporated into) head mount 10 in a predetermined pattern, with each device in the kit providing a different predetermined pattern of magnet assemblies 15.

These and other changes will be apparent to those skilled in the art in view of the present disclosure and are considered to be within the scope of the present invention.

What is claimed is:

1. An apparatus for applying Transcranial Magnetic Stimulation (TMS) to a patient, wherein the apparatus comprises:
    a head mount for disposition on the head of the patient; and
    a plurality of magnet assemblies for releasable mounting on the head mount, wherein each of the magnet assemblies comprises a permanent magnet configured to selectively provide a rapidly changing magnetic field of 500-5000 Tesla/second, corresponding to a magnet movement speed of no less than 400 Hertz, capable of inducing electric currents in the brain of the patient so as to modify natural electrical activity of the brain of the patient, wherein the apparatus causes movement of the permanent magnets to effect the rapidly changing magnetic fields; and wherein the permanent magnets are each operated to provide a magnetic field having certain spatial, strength, and temporal characteristics;
    wherein the number of magnet assemblies mounted on the head mount, their individual positioning on the head mount, and their selective provision of the rapidly changing magnetic fields is selected so as to allow spatial, strength, and temporal characteristics of the magnetic field to be custom tailored for the patient, whereby to provide patient-specific TMS therapy, to assist in diagnosis or to map out brain function in neuroscience research.

2. The apparatus according to claim 1, wherein the head mount comprises a skull cap.

3. The apparatus according to claim 1, wherein the magnet assemblies are secured to the head mount using a hook-and-loop fastener.

4. The apparatus according to claim 3, wherein the hook-and-loop fastener comprises a fastener base disposed on the head mount and a fastener connect disposed on each of the magnet assemblies.

5. The apparatus according to claim 1, wherein the magnet assemblies comprise an apparatus for moving the permanent magnet.

6. The apparatus according to claim 5, wherein the apparatus for moving the permanent magnet comprises a motor, and further wherein the permanent magnet is attached to a drive shaft of the motor.

7. The apparatus according to claim 5, wherein the apparatus for moving the permanent magnet comprises a solenoid.

8. The apparatus according to claim 5, wherein the permanent magnet comprises a rare earth magnet.

9. The apparatus according to claim 8, wherein the rare earth magnet comprises neodymium.

10. The apparatus according to claim 1, further comprising a computerized controller for selectively causing selected ones of the magnet assemblies to provide a rapidly changing magnetic field.

11. The apparatus according to claim 1, further comprising a plurality of electrodes for monitoring the natural electrical activity of the brain.

12. A method for providing Transcranial Magnetic Stimulation (TMS) to a patient, the method comprising: providing an apparatus comprising:
  a head mount for disposition on the head of the patient; and
  a plurality of magnet assemblies for releasable mounting on the head mount, wherein each of the magnet assemblies comprises a permanent magnet configured to selectively provide a rapidly changing magnetic field of 500-5000 Tesla/second, corresponding to a magnet movement speed of no less than 400 Hertz, capable of inducing electric currents in the brain of the patient so as to modify natural electrical activity of the brain of the patient,
  positioning the head mount on the head of the patient, and positioning a selected number of magnet assemblies on the head mount at selected locations; and
  selectively moving at least some of the magnet assemblies to provide the rapidly changing magnetic fields, wherein the permanent magnets are each operated to provide a magnetic field having certain spatial, strength, and temporal characteristics;
  wherein the number of magnet assemblies mounted on the head mount, their individual positioning on the head mount, and their selective provision of the rapidly changing magnetic fields is selected so as to custom tailor the spatial, strength, and temporal characteristics of the magnetic field for the patient, whereby to provide patient-specific TMS therapy, to assist in diagnosis or to map out brain function in neuroscience research.

13. The method according to claim 12, wherein the head mount comprises a skull cap.

14. The method according to claim 12, wherein the magnet assemblies are secured to the head mount using a hook-and-loop fastener.

15. The method according to claim 14, wherein the hook-and-loop fastener comprises a fastener base disposed on the head mount and a fastener connect disposed on each of the magnet assemblies.

16. The method according to claim 12, wherein the magnet assemblies comprise an apparatus for moving the permanent magnet.

17. The method according to claim 16, wherein the apparatus for moving the permanent magnet comprises a motor, and further wherein the permanent magnet is attached to a drive shaft of the motor.

18. The method according to claim 16, wherein the apparatus for moving the permanent magnet comprises a solenoid.

19. The method according to claim 16, wherein the permanent magnet comprises a rare earth magnet.

20. The method according to claim 19, wherein the rare earth magnet comprises neodymium.

21. The method according to claim 12, further comprising a computerized controller for selectively causing selected ones of the magnet assemblies to provide a rapidly changing magnetic field.

22. The method according to claim 12, further comprising a plurality of electrodes for monitoring the natural electrical activity of the brain.

* * * * *

UNITED STATES PATENT AND TRADEMARK OFFICE
CERTIFICATE OF CORRECTION

PATENT NO. : 10,500,408 B2
APPLICATION NO. : 15/281475
DATED : December 10, 2019
INVENTOR(S) : Santosh A. Helekar et al.

It is certified that error appears in the above-identified patent and that said Letters Patent is hereby corrected as shown below:

On the Title Page

In the Abstract
At item (57), Line 5, "comprises" should be -- comprise --.
On Page 2, at item (57), Line 3, "assembles" should be -- assemblies --.
On Page 2, at item (57), Line 4, "for provide" should be -- for providing --.

Signed and Sealed this
Seventh Day of July, 2020

Andrei Iancu
*Director of the United States Patent and Trademark Office*